United States Patent
Nöcker et al.

(10) Patent No.: US 12,383,480 B2
(45) Date of Patent: Aug. 12, 2025

(54) DYEING METHOD FOR KERATIN FIBERS COMPRISING A DIRECT AZO-DYE AND AN ORGANIC ALKALIZING AGENT, AND KIT-OF-PARTS THEREOF

(71) Applicant: KAO CORPORATION, Tokyo (JP)

(72) Inventors: Bernd Nöcker, Darmstadt (DE); Steven Breakspear, Darmstadt (DE); Fariba Ghiasi, Darmstadt (DE); Anna Neu, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 18/716,616

(22) PCT Filed: Dec. 20, 2022

(86) PCT No.: PCT/EP2022/086937
§ 371 (c)(1),
(2) Date: Jun. 5, 2024

(87) PCT Pub. No.: WO2023/118103
PCT Pub. Date: Jun. 29, 2023

(65) Prior Publication Data
US 2025/0041181 A1    Feb. 6, 2025

(30) Foreign Application Priority Data
Dec. 23, 2021 (EP) ................................ 21217424

(51) Int. Cl.
| | |
|---|---|
| *A61Q 5/10* | (2006.01) |
| *A61K 8/41* | (2006.01) |
| *A61K 8/49* | (2006.01) |
| *A61Q 5/06* | (2006.01) |

(52) U.S. Cl.
CPC ............... *A61K 8/41* (2013.01); *A61K 8/494* (2013.01); *A61Q 5/065* (2013.01); *A61Q 5/10* (2013.01); *A61K 2800/4322* (2013.01); *A61K 2800/4324* (2013.01); *A61K 2800/88* (2013.01)

(58) Field of Classification Search
CPC .. A61K 8/41; A61K 8/494; A61K 2800/4322; A61K 2800/4324; A61K 2800/88; A61K 8/411; A61Q 5/065; A61Q 5/10
USPC ............................................................ 8/405
See application file for complete search history.

(56) References Cited

U.S. PATENT DOCUMENTS

| 4,834,768 A | 5/1989 | Grollier |
| 2010/0146716 A1* | 6/2010 | Yamaguchi ............ A61Q 5/065 8/405 |
| 2020/0197269 A1* | 6/2020 | Gasselin .................. A61Q 5/08 |
| 2020/0289389 A1* | 9/2020 | Monda ................... A61K 8/494 |

FOREIGN PATENT DOCUMENTS

| EP | 1 366 752 A1 | 12/2003 | |
| EP | 2 979 683 A1 | 2/2016 | |
| EP | 3 427 720 A1 | 1/2019 | |
| EP | 3685820 A1 * | 7/2020 | ............. A61Q 5/065 |
| WO | WO 2019057829 A1 * | 3/2019 | ............... A61Q 5/10 |
| WO | WO 2021028532 A1 * | 2/2021 | ............. A61Q 5/065 |

OTHER PUBLICATIONS

International Search Report & Written Opinion issued Mar. 31, 2023 in PCT/EP2022/086937, filed on Dec. 20, 2022, 11 pages.
European Search Report issued Jun. 17, 2022 in EP application 21217424.7, filed on Dec. 23, 2021, 9 pages.
Database GNPD [Online] Mintel ; Aug. 29, 2007 (Aug. 29, 2007), anonymous: "Blonde Kit", XP055932572, Database accession No. 755614, 3 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A method for dyeing keratin fibers, including mixing an aqueous dyeing composition containing a dye compound which is an anionic azo dye, a non-ionic azo dye, a salt thereof, or a mixture thereof, and an alkalizing agent having at least one basic functional group whose conjugated acid has a pKa value in a range of 6.0 to 8.0, with a second aqueous composition having a pH in a range of 1 to 6 to yield a ready-to-use composition having a pH in a range of 7 to 12. The method further includes applying the ready-to-use composition onto the keratin fibers and leaving it for a time period in a range of 1 min to 60 min, and rinsing-off the keratin fibers. The alkalizing agent is triethanolamine, 2-[4-(2-hydroxyethyl)-piperazin-1-yl]-ethane-1-sulfonic acid, a salt thereof, or a mixture thereof.

20 Claims, No Drawings

DYEING METHOD FOR KERATIN FIBERS COMPRISING A DIRECT AZO-DYE AND AN ORGANIC ALKALIZING AGENT, AND KIT-OF-PARTS THEREOF

CROSS REFERENCE TO RELATED APPLICATIONS

This application is a National Stage entry under 35 U.S.C. § 371 of PCT/EP2022/086937, filed on Dec. 20, 2022, and claims priority to European Patent Application No. 21217424.7, filed on Dec. 23, 2021. The entire contents of both are incorporated herein by reference.

FIELD OF THE INVENTION

The present invention is directed to a dyeing method for keratin fibers comprising certain direct dyes and particular alkalizing agents, and a kit-of-parts.

BACKGROUND OF THE INVENTION

Direct dyes have been of particular interest to the cosmetic industry over the past decade. In contrast to their oxidative counterparts, direct dyes are easier to apply to keratin fibers, but often lack durability on keratin fibers. In addition, on grey hair, direct dyes often lack dyeing intensity when used without oxidative dyes.

Applicant has developed new direct dyes (EP1366752), which complement the availability and color range of existing dyes. A series of the aforementioned developed dyes comprises HC Blue 18, HC Red 18, and HC Yellow 16.

EP2979683 discloses tris-(hydroxymethyl)-aminomethane as alkalizing agent for oxidative dyeing compositions and generally discloses the combination with direct dyes. Improved evenness of coloration with oxidative dyes has been found.

The prior art, however, has not satisfactorily solved the dyeing intensity and durability challenge of direct dyes, and, therefore, there is a real need to develop direct dyeing compositions for keratin fibers, which have improved dyeing intensity and durability, in particular on hair with prior hair damage.

SUMMARY OF THE INVENTION

Therefore, the first object of the present invention is a method for dyeing keratin fibers, preferably human keratin fibers, more preferably human hair, comprising the steps of:
i) mixing an aqueous dyeing composition A comprising
a) one or more anionic or non-ionic azo dye(s) and/or their salt(s), and/or their mixture(s),
b) one or more alkalizing agent(s) having at least one basic functional group whose conjugated acid has a pKa value in the range of 6.0 to 8.0 determined by acid-base titration in water of a 0.1 M solution of the alkalizing agent at 20° C. under atmospheric conditions,
with a second aqueous composition C having a pH in the range of 1 to 6 and optionally comprising one or more oxidizing agent(s), preferably hydrogen peroxide, to yield a ready-to-use composition having a pH in the range of 7 to 12,
ii) applying the ready-to-use composition onto keratin fibers and leaving it for a time period in the range of 1 min to 60 min,
iii) rinsing-off the keratin fibers and optionally shampooing the keratin fibers,
wherein the one or more compound(s) according to group b) is/are triethanolamine, 2-[4-(2-hydroxyethyl)-piperazin-1-yl]-ethane-1-sulfonic acid, and/or their salt(s), and/or their mixtures.

The second object of the present invention is a kit-of-parts comprising
an aqueous dyeing composition A as defined above,
a composition B comprising one or more direct dye(s) selected from HC Yellow 1, and/or 2-amino-6-chloro-4-nitrophenol, and/or their salt(s), and/or their mixtures, and
composition C as defined above having a pH in the range of 1 to 6 and optionally comprising one or more oxidizing agent(s), preferably hydrogen peroxide.

DETAILED DESCRIPTION OF THE INVENTION

Inventors of the present invention have surprisingly found that dyeing intensity, durability, and wash fastness of certain direct dyes is improved in the presence of certain organic alkalizing agents having at least one basic function whose conjugate acid has a pKa in the range of 6.0 to 8.0. Moreover, such an inventive dyeing composition improves cosmetic properties of keratin fibers such as feel, shine, and touch.

Dyeing Method

The present invention is directed to a method for dyeing keratin fibers, preferably human keratin fibers, more preferably human hair, comprising the steps of:
i) mixing an aqueous dyeing composition A comprising
a) one or more anionic or non-ionic azo dye(s) and/or their salt(s), and/or their mixture(s),
b) one or more alkalizing agent(s) having at least one basic functional group whose conjugated acid has a pKa value in the range of 6.0 to 8.0 determined by acid-base titration in water of a 0.1 M solution of the alkalizing agent at 20° C. under atmospheric conditions,
with a second aqueous composition C having a pH in the range of 1 to 6 and optionally comprising one or more oxidizing agent(s), preferably hydrogen peroxide, to yield a ready-to-use composition having a pH in the range of 7 to 12,
ii) applying the ready-to-use composition onto keratin fibers and leaving it for a time period in the range of 1 min to 60 min,
iii) rinsing-off the keratin fibers and optionally shampooing the keratin fibers,
wherein the one or more compound(s) according to group b) is/are triethanolamine, 2-[4-(2-hydroxyethyl)-piperazin-1-yl]-ethane-1-sulfonic acid, and/or their salt(s), and/or their mixtures.

It is preferred from the viewpoint of wash fastness that one or more anionic or non-ionic azo dye(s) according to group a) is/are HC Red 18, HC Blue 18, HC Yellow 16, Disperse Black 9, Acid Black 1, Disperse Orange 3, Disperse red 17, Acid black 52, Acid Red 14, Acid Orange 7, Acid Red 27, Acid Red 33, Acid Red 35, Acid Red 184, Acid Yellow 23, Acid Orange 24, Solvent Red 1, Curry Red, Acid Red 18, Pigment Red 57, and/or their salt(s), and/or their mixtures, preferably it is HC Red 18, HC Blue 18, HC Yellow 16, Disperse Black 9, and/or their salt(s), and/or their mixture(s).

It is preferred from the viewpoint of dyeing intensity that the total concentration of compound(s) according to group a) is 0.001% by weight or more, more preferably 0.002% by weight or more, further more preferably 0.05% by weight or more, still further more preferably 0.1% by weight or more, calculated to the total weight of the composition A.

It is preferred from the viewpoint of economic reasons and cosmetic safety that the total concentration of compound(s) according to group a) is 10% by weight or less, more preferably 0.5% by weight or less, further more preferably 2% by weight or less, still further more preferably 1% by weight or less, calculated to the total weight of the composition A.

For attaining the above-mentioned effects, it is preferred that the total concentration of compound(s) according to group a) is in the range of 0.001% to 10% by weight, preferably in the range of 0.002% to 5% by weight, more preferably in the range of 0.05% to 2% by weight, still further more preferably 0.1% to 1% by weight, calculated to the total weight of the composition A.

Composition A comprises one or more alkalizing agent(s) having at least one basic functional group whose conjugated acid has a pKa value in the range of 6.0 to 8.0 determined by acid-base titration in water of a 0.1 M solution of the alkalizing agent at 20° C. under atmospheric conditions. The one or more alkalizing agent(s) of composition A is/are triethanolamine (pKa 7.7), 2-[4-(2-hydroxyethyl)-piperazin-1-yl]-ethane-1-sulfonic acid (pKa 7.4), and/or their salt(s), and/or their mixtures.

Preferably, the pKa range of the conjugate acid of the at least one basic function is in the range of 7.0 to 8.0 measured, as disclosed above.

Suitable acids for titration are strong acids with a pKa of 1 or less. Suitable strong acids are trifluoracetic acid, nitric acid, sulfuric acid, hydrochloric acid, hydrobromic acid, hydroiodic acid, and/or perchloric acid. Titration is conducted in water.

A suitable means for detection is an electrode, suitably a pH sensitive electrode or an electrode registering the conductivity change of the titration environment.

Suitably, a titration at 0.1 M solution of the alkalizing agent is conducted at 20° C. and under atmospheric conditions in water. A suitable strong acid concentration is, for example, a 6 M solution of hydrochloric acid.

It is preferred from the viewpoint of wash fastness that one or more compound(s) according to group b) is/are selected from triethanolamine and/or its salt(s), more preferably one or more compound(s) according to group b) is/are selected from triethanolamine and/or its inorganic salt(s), still more preferably one or more compound(s) according to group b) is/are selected from triethanolamine and/or its hydrochloride, sulfate, hydrosulfate, nitrate salt(s).

It is preferred from the viewpoint of dyeing intensity that the total concentration of compound(s) according to group b) is 0.1% by weight or more, more preferably 0.25% by weight or more, further more preferably 0.5% by weight or more, still further more preferably 0.75% by weight or more, still further more preferably 1% by weight or more, calculated to the total weight of composition A.

It is preferred from the viewpoint of economic reasons and cosmetic safety that the total concentration of compound(s) according to group b) is 40% by weight or less, more preferably 30% by weight or less, further more preferably 20% by weight or less, still further more preferably 15% by weight or less, calculated to the total weight of composition A.

For attaining the above-mentioned effects, it is preferred that the total concentration of compound(s) according to group b) is in the range of 0.1% to 40% by weight, preferably in the range of 0.25% to 30% by weight, more preferably in the range of 0.5% to 20% by weight, more preferably in the range of 0.75% to 15% by weight, calculated to the total weight of composition A.

It is further preferred from the viewpoint of dyeing intensity, that the weight ratio of compound(s) according to group b) to compound(s) according to group a) in composition A is 0.1 or more, more preferably 0.5 or more, further more preferably 1 or more, still further more preferably 1.5 or more, still more preferably 5 or more, further still more preferably 10 or more.

It is further preferred from the viewpoint of dyeing intensity, formulation stability, and cosmetic safety that the weight ratio of compound(s) according to group b) to compound(s) according to group a) in composition A is 200 or less, more preferably 180 or less, further more preferably 150 or less, still further more preferably 125 or less, still further more preferably 100 or less, still further more preferably 75 or less.

For attaining the above-mentioned effects, it is preferred that the weight ratio of compound(s) according to group b) to compound(s) according to group a) in composition A is in the range of 0.1 to 200, preferably in the range of 0.5 to 180, more preferably in the range of 1 to 150, further more preferably in the range of 1.5 to 125, still more preferably in the range of 5 to 100, still more preferably in the range of 10 to 75.

Cosmetic Form of Composition A

Composition A is an aqueous composition. The term 'aqueous' denotes a composition A that comprises a majority of water, i.e., the composition preferably comprises water at 50% by weight or more, further more preferably at 60% by weight or more, still more preferably at 70% by weight or more, still further more preferably at 80% by weight or more, calculated to the total weight of composition A, from the viewpoint of achieving a cosmetically acceptable composition A.

It is further preferred from the viewpoint of dyeing intensity that composition A comprises water at 98% by weight or less, more preferably at 95% by weight or less, further more preferably at 92% by weight or less, calculated to the total weight of composition A.

For achieving the above-mentioned effects, it is preferred that the total concentration of water in composition A is in the range of 50% to 98% by weight, more preferably in the range of 60% to 95% by weight, further more preferably in the range of 70% to 92% by weight, still more preferably in the range of 80% to 92% by weight, calculated to the total weight of composition A.

It is preferred from the viewpoint of dyeing performance that the pH of composition A is 7 or more, more preferably the pH is 7.5 or more, further more preferably the pH is 8 or more, still further more preferably the pH is 8.5 or more.

It is preferred from the viewpoint of hair damage and dyeing performance that the pH of composition A is 12 or less, more preferably the pH is 11 or less, still more preferably the pH is 10.5 or less.

For attaining the above-mentioned effects, it is preferred that the composition A has a pH in the range of 7 to 12, preferably in the range of 7.5 to 11, more preferably in the range of 8 to 10.5, further more preferably in the range of 8.5 to 10.5.

All pH values are measured at 20° C. under atmospheric conditions with a suitable means such as a pH sensitive electrode.

In one aspect of the present invention, composition A may comprise one or more organic solvent(s) according to group c). For this aspect, suitable concentrations of compound(s) according to group c) are in the range of 0.1% to 10% by weight, calculated to the total weight of composition A. Suitable solvents are mono-, di-, and trivalent alcohols and/or their mixtures.

Suitable mono-, di-, and trivalent alcohols from the viewpoint of cosmetic safety and dissolution capacity are ethanol, n-propanol, isopropanol, propylene glycol, ethylene glycol, benzyl alcohol, phenoxyethanol, and glycerol, and/or their mixtures.

Lipophilic Compounds According to Group d)

It is preferred from the viewpoint of further increasing dyeing intensity that composition A comprises one or more lipophilic compound(s) being liquid at 25° C. under atmospheric pressure as compound(s) according to group d).

Suitable compounds according to group d) are natural and/or vegetable oils, petrolatum-based compounds, linear or branched, saturated or unsaturated fatty alcohols with C12 to C22, and fatty acid esters consisting of linear or branched, saturated or unsaturated fatty acids with C12 to C22 being esterified with linear or branched primary alcohols with C3 to C12, and silicones.

Suitable natural and/or vegetable oils are olive oil, almond oil, avocado oil, wheatgerm oil, and castor oil.

Suitable petrolatum-based compounds are liquid paraffins, especially paraffinum perliquidum and paraffinum subliquidum, and mineral oil, in particular white mineral oil.

Suitable comprises fatty compounds selected from linear or branched, saturated or unsaturated fatty alcohols with C12 to C22 are lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, behenyl alcohol, and/or their mixtures, such as cetearyl alcohol.

Suitable examples for fatty acid esters consisting of linear or branched, saturated or unsaturated fatty acids with C12 to C22 being esterified with linear or branched primary alcohols with C3 to C18 are octyl palmitate, isocetyl palmitate, isopropyl palmitate, octyl stearate, oleyl oleate, and myristyl myristate, as well as their mixtures.

Suitably, the compositions may also comprise lipophilic ingredients such as silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; C10- to C36-fatty acid triglycerides, as well as their mixtures.

It is further preferred from the viewpoint of further increasing dyeing intensity that composition A is an emulsion and comprises one or more compound(s) according to group d) selected from fatty alcohols having an branched or linear, saturated or unsaturated carbon chain length in the range of C12 to C22, fatty acids having an branched or linear, saturated or unsaturated carbon chain length in the range of C12 to C22, ester oils, vegetable oils, silicone oil, paraffin oils.

Suitable concentrations of compound(s) according to d) in emulsions range from 0.5% to 20% by weight, preferably from 1% to 10% by weight, calculated to the total weight of composition A.

Surfactants

It is further preferred from the viewpoint of composition stability and mixability as well as wetting of keratin fibers that composition A further comprises one or more surfactant(s) as compound(s) according to f), more preferably selected from non-ionic, cationic, anionic, zwitterionic/amphoteric surfactant(s).

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric/zwitterionic surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate are also suitable.

Typical cationic surfactants are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

It is preferred from the viewpoint of composition stability, wetting of keratin fibers, and ingredient dispersibility that the total concentration of compound(s) according to f) in composition A is 0.1% by weight or more, preferably 0.2% by weight or more, further more preferably 0.25% by weight or more, calculated to the total weight of composition A.

It is preferred from the viewpoint of composition stability, wetting of keratin fibers, and ingredient dispersability that the total concentration of compound(s) according to f) in composition A is 5% by weight or less, preferably 4% by weight or less, further more preferably 2.5% by weight or less, calculated to the total weight of composition A.

For attaining the above-mentioned effects, it is preferred that the total concentration of compound(s) according to f) in composition A is in the range of 0.1% to 5% by weight, more preferably 0.2% to 4% by weight, further more preferably 0.2% to 2.5% by weight, calculated to the total weight of composition A.

Alkalizing Agent(s) Different from Group b)

It is preferred from the viewpoint of high pH dyeing that composition A comprises one or more alkalizing agents different from compound(s) according to group b), preferably selected from ammonia and/or its salt(s), organic alkyl and/or alkanolamines having at least one basic function whose conjugate acid has a pKa above 8.0 determined by acid-base titration in water of a 0.1 M solution of the alkalizing agent at 20° C. under atmospheric conditions, and/or their salt(s), and/or their mixture(s).

Suitable organic alkyl and/or alkanolamines and/or their salt(s) are according to the following general structure:

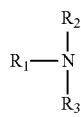

wherein R1, R2, and R3 are independently selected from H, linear C1-C6 alkyl which may be substituted with one hydroxyl group, or branched C3-C12 alkyl or alkanol, wherein at least one of R1, R2, or R3 is different from H, and/or their salts, and/or their mixtures.

Suitably, one or more alkyl and/or alkanolamine(s) and/or its/their salt(s), are selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, and/or its/their salt(s), and/or their mixtures, from the viewpoint of providing alkalinity and cosmetic safety as well as their low odor.

The preferred alkalizing agents different from compound(s) according to group b) is/are selected from ammonia, monoethanolamine, 2-amino-2-methylpropanol, and/or its/their salt(s), and/or their mixtures, from the viewpoint of providing alkalinity and cosmetic safety.

It is preferred from the viewpoint of providing alkalinity that the total concentration of alkalizing agents different from compound(s) according to group b) is 0.1% by weight or more, more preferably 0.25% by weight or more, further more preferably 0.4% by weight or more, calculated to the total weight of composition A.

It is preferred from the viewpoint of providing alkalinity, hair damage, and odor that the total concentration of alkalizing agents different from compound(s) according to group b) is 40% by weight or less, more preferably 30% by weight or less, further more preferably 25% by weight or less, calculated to the total weight of composition A.

For attaining the above-mentioned effects, it is preferred that the total concentration of alkalizing agents different from compound(s) according to group b) in composition A is in the range of 0.1% to 40% by weight, preferably in the range of 0.25% to 30% by weight, more preferably in the range of 0.4% to 25% by weight, calculated to the total weight of composition A.

Other Direct Dyes Different from the Ones of Group a)

In one aspect of the present invention, composition A may comprise one or more direct dye(s) different from the ones according to group a).

Suitable direct dyes may be selected from cationic, anionic and/or non-ionic direct dyes.

The most preferred direct dye(s) different from the ones according to group a) are HC Yellow 1,2-amino-6-chloro-4-nitrophenol, and/or their salt(s), and/or their mixture(s), from the viewpoint of improving wash fastness of the composition.

The total concentration of one or more direct dyes other than the ones of groups a) in composition A, if present, preferably is 0.01% by weight or more, more preferably 0.05% by weight or more, further more preferably 0.1% by weight or more, calculated to the total weight of composition A, from the viewpoint of wash fastness.

The total concentration of one or more direct dyes other than the ones of groups a) and b) in composition A, if present, preferably is 10% by weight or less, more preferably 9% by weight or less, further more preferably 7.5% by weight or less, further more preferably 6% by weight or less, even more preferably 4% by weight or less, calculated to the total weight of the composition, from the viewpoint of economic reasons and wash fastness.

For attaining the above-mentioned effects, the total concentration of one or more direct dyes other than the ones of groups a) in composition A, if present, is in the range of 0.01% to 10% by weight, preferably 0.05% to 9% by weight, more preferably 0.1% to 7.5% by weight, further more preferably 0.1% to 6% by weight, even more preferably 0.1% to 4% by weight, calculated to the total weight of composition A.

Oxidative Dyes

Composition A may further comprise one or more oxidative dye(s). Oxidative dyes are classified as oxidative dye couplers and oxidative dye precursors.

The term 'precursor' within the meaning of the present invention denotes a compound that is oxidized by an oxidizing agent prior to its reaction with at least another compound, preferably with at least another coupler compound.

The term 'coupler' within the meaning of the present invention denotes a compound that is able to react with the oxidized precursor to form a dye intermediate. The couple itself is not oxidizing prior to reaction with the precursor.

Suitable oxidative dye precursors classes are p-phenylenediamines, p-aminophenols, and heterocyclic compounds such as diaminopyrazols and substituted pyrimidines, and suitable coupling substances are resorcinols, m-aminophenols, m-phenylenediamines, pyridines and substituted derivatives, and naphthols.

Suitable oxidative dye couplers are 5-amino-2-methylphenol, 2-methyl-5-hydroxyethylaminophenol, 2,4,-diaminophenoxyethanol, 2-amino-4-hydroxyethylaminoanisole, 2-methyl-5-amino-6-chlorophenol, 1,3-bis(2,4-diaminophenoxy) propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N, N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxy-ethyl) amino] benzene, α-naphthol, 4,6-dichlororesorcinol, 1,3-diaminotoluene, 4-hydroxy-1,2-methylenedioxy benzene, 1,5- dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)-benzene, and/or their salts, and/or their mixtures.

Composition A may comprise oxidative dyes at approximately the equimolar proportions, for example at a total concentration in the range of 0.001% to 5%, calculated to the total weight of composition A.

Thickening Polymers

It is advantageous from the viewpoint of cosmetic safety that composition A further comprises one or more thickening polymer(s).

Preferably, the thickening polymers are selected from polymers resulting in an aqueous solution and/or aqueous dispersion at pH between 8 and 10 having a viscosity of at least 5,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as (C2-C8)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch-based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers in composition A is 0.1% by weight or more, more preferably 0.25% by weight or more, more preferably 0.5% by weight or more, calculated to the total weight of the composition, from the viewpoint of providing sufficient viscosity to composition A.

Preferably, the total concentration of thickening polymers of composition A is 15% by weight or less, more preferably 12% by weight or more, further more preferably 10% by weight or less, calculated to the total weight of composition A, from the viewpoint of providing sufficient viscosity to the composition and cost of goods.

For attaining the above-mentioned effects, it is preferred that the total concentration of thickening polymers in composition A is in the range of 0.1% to 15% by weight, preferably 0.25% to 12% by weight, more preferably in the range of 0.5% to 10% by weight, calculated to the total weight of composition A.

Two-Part Dyeing Composition

In one aspect of the present invention, the composition may be part of a two-part dyeing composition characterized in that the first part is composition A as defined above, and the second composition is an aqueous second composition C having a pH in the range of 1 to 6 and optionally comprising one or more oxidizing agent(s).

The second aqueous composition C preferably comprises hydrogen peroxide as an oxidizing agent. Suitable concentrations range from 0.1% to 20% by weight, preferably 0.25% to 15% by weight, and more preferably 0.5% to 12% by weight, calculated to the total weight of the second aqueous composition C.

The pH of the second aqueous composition C preferably is in the range of 1.5 to 5, more preferably in the range of 2 to 4.5, adjusted by suitable acids and bases.

It is further preferred from the viewpoint of mixability with composition A that the composition C comprises one or more lipophilic compound(s) according to e), as laid out above for composition A. In such a case, the composition C is an emulsion and preferably also comprises one or more surfactant(s) as compound(s) according to f), as laid out above for composition A.

Compositions A and C in this aspect of the present invention are intended to be mixed directly prior to application onto keratin fibers.

Kit-of-Parts

The present invention is also directed to a kit-of-parts comprising an aqueous dyeing composition A as defined above, a composition B comprising one or more direct dye(s) selected from HC Yellow 1, and/or 2-amino-6-chloro-4-nitrophenol, and/or their salt(s), and/or their mixtures, and a composition C as defined above having a pH in the range of 1 to 6 and optionally comprising one or more oxidizing agent(s), preferably hydrogen peroxide.

Composition B may be a dyeing composition comprising one or more alkalizing agent(s) and having a pH in the range of 7 to 12.

The composition B, however, may also be a cleansing and/or conditioning composition for keratin fibers, preferably comprising one or more surfactant(s) and one or more direct dye(s) selected from HC Yellow 1 and/or 2-amino-6-chloro-4-nitrophenol, and/or their salt(s), and/or their mixtures. Suitable concentrations for these dyes are explained above under the section of other direct dyes different from the ones of group a). For example, it is preferred from the viewpoint of wash fastness that the total concentration of HC Yellow 1, and/or 2-amino-6-chloro-4-nitrophenol, and/or their salt(s), and/or their mixtures is in the range of 0.01% to 10% by weight, preferably in the range of 0.02% to 5% by weight, more preferably in the range of 0.05% to 2% by weight, calculated to the total weight of composition B.

It is preferred from the viewpoint of color intensity that the pH of the ready-to-use composition as defined in step i) is in the range of 8 to 11, more preferably in the range of 8.5 to 10.5.

It is further preferred from the viewpoint of dyeing intensity and dyeing method economy that the leave-on time as defined in step ii) is in the range of 2 min to 45 min, more preferably in the range of 5 min to 40 min, further more preferably in the range of 10 min to 30 min.

EXAMPLES

TABLE 1

|  |  | Ingredients | Inv. Ex. 1 | Inv. Ex. 2 | Inv. Ex. 3 | Compar. Ex. 1 | Compar. Ex. 2 | Compar. Ex. 3 | Compar. Ex. 4 |
|---|---|---|---|---|---|---|---|---|---|
| Composition A | a) | HC Blue 18 | 0.135 | 0.135 | — | 0.135 | 0.135 | 0.135 | — |
|  |  | HC Red 18 | 0.015 | 0.015 | — | 0.015 | 0.015 | 0.015 | — |
|  |  | HC Yellow 16 | 0.25 | 0.1 | — | 0.25 | 0.25 | 0.25 | — |
|  |  | Disperse Black 9 | — | 0.1 | — | — | — | — | — |
|  |  | Acid Red 14 | — | — | 0.2 | — | — | — | 0.2 |
|  |  | Acid Yellow 1 | — | 0.5 | — | — | — | — | — |
|  | b) | Triethanolamine (pKa 7.7) | 5.0 | 4.0 | 5.0 | — | — | — | — |
|  |  | 2-Aminomethyl propanol (pKa 9.7) | — | — | — | 5.0 | — | — | 5.0 |
|  |  | Ammonia 25% w/w (pKa 9.2) | — | 1.0 | — | — | 2.0 | — | — |
|  |  | Sodium bicarbonate | — | — | — | — | 3.4 | — | — |
|  |  | Sodium metasilicate | — | — | — | — | — | 4.9 | — |
|  |  | Water | Ad 100.0 | | | | | | |
| Evaluation |  | Intensity directly upon dyeing, $\Delta E^*_{a,b}$ | 68.42 | 66.19 | 62.57 | 63.05 | 62.95 | 60.80 | 54.46 |
|  |  | Upon washing, $\Delta E^*_{a,b}$ | 68.03 | 63.50 | 38.64 | 54.80 | 59.67 | 48.59 | 24.24 |
|  |  | Color loss/wash fastness, $\Delta\Delta E^*_{a,b}$ | 0.39 | 2.69 | 23.92 | 8.25 | 3.28 | 12.21 | 30.22 |

The pH of the above compositions was 9.5 ± 0.3. The amount of sodium bicarbonate and sodium metasilicate in the comparative examples are the molar equivalent amounts, relative to the other alkalizing agents.

Discussion of Results

The examples of table 1 illustrate, that higher color intensities (high $\Delta E^*_a b$ values) were achieved with the inventive examples with respect to the comparative example. This is particularly relevant for inventive example 1 and comparative example 2.

Inventive example 1 showed superior color intensity and wash fastness ($\Delta\Delta E^*_a b$ values) with respect to comparative example 1, which replaces the same amount of triethanolamine with AMP.

Inventive example 2 showed superior wash fastness with respect to comparative example 1, which replaces a part of the triethanolamine with ammonia.

The dyeing intensity and wash fastness were both improved with the inventive composition comprising Acid Red 14.

Methods

Hair Preparation

Commercially available goat hair (10 cm long, 2 g per bundle) was pre-washed and blow-dried prior to any treatment. A commercial bleaching treatment was performed, which is available under the trade name SilkLift Strong, under the brand name Goldwell. The first step was the application of a reducing composition comprising thioglycolic acid, leaving it for 20 min on the hair, then rinsing it off and applying an oxidizing composition comprising hydrogen peroxide. The oxidizing composition was left for 15 min onto the hair and then the hair was shampooed and blow-dried. The hair obtained by this method was used for the dyeing experiments on permed hair.

Hair Dyeing

To prepare a ready-to-use composition, each of the compositions from above were mixed with a second acidic composition C having a pH of 2.5 in a weight ratio of 1:1. 2 g of the resulting ready-to-use compositions were applied to the hair as prepared above and left for 20 min at ambient temperature. The hair was then rinsed-off with water and blow-dried.

Colorimetric measurements (Datacolor 45G, Datacolor AG Europe, Rotkreuz, Switzerland) were conducted on the hair streaks with a color-difference meter using the CIE colorimetric system (L*, a*, b*). They are termed 'freshly-colored' (1) for further calculation purposes.

Wash Fastness Experiments

Each hair streak was then placed in a shaking bath comprising a 1.5% by weight solution of sodium laureth sulfate at 40° C. and 100 rpm for 30 min. Then the hair streaks were rinsed-off with water and blow dried. Colorimetric measurements were conducted again and the (L*, a*, b*) values were obtained. They are termed 'washed' (2) for further calculation purposes.

$\Delta E^*_{a,b}$ Calculations

For assessing the color differences between washed (2) and freshly colored hair (1), each L*, a*, and b* values of the samples were obtained.

$\Delta E^*$ was then calculated by the following equation:

$$\Delta E^*_{a,b} = \sqrt{(L^*_2 - L^*_1)^2 + (a^*_2 - a^*_1)^2 + (b^*_2 - b^*_1)^2}$$

The following examples are within the scope of the present invention.

Example 4

|  | % by weight |
|---|---|
| HC Blue 18 | 0.1 |
| HC Red 18 | 0.05 |
| HC Yellow 16 | 0.08 |
| Triethanolamine | 0.8 |
| 2-Aminomethyl propanol | 2.5 |
| Ceteareth-30 | 3.0 |
| Sodium lauryl sulfate | 1.5 |
| Cetearyl alcohol | 4.0 |
| Benzyl alcohol | 1.0 |
| Acrylates copolymer | 1.5 |
| NaOH/HCl | ad pH 9.5 |
| Water | ad 100.0 |

The invention claimed is:

1. A method for dyeing keratin fibers, comprising:
   mixing an aqueous dyeing composition comprising a dye compound which is an anionic azo dye, a non-ionic azo dye, a salt thereof, or a mixture thereof, and an alkalizing agent having at least one basic functional group whose conjugated acid has a pKa value in a range of 6.0 to 8.0 determined by acid-base titration in water of a 0.1 M solution of the alkalizing agent at 20° C. under atmospheric conditions, with a second aqueous composition having a pH in a range of 1 to 6 to yield a ready-to-use composition having a pH in a range of 7 to 12;
   applying the ready-to-use composition onto the keratin fibers and leaving it for a time period in a range of 1 min to 60 min; and
   rinsing-off the keratin fibers,
   wherein the alkalizing agent is triethanolamine, 2-[4-(2-hydroxyethyl)-piperazin-1-yl]-ethane-1-sulfonic acid, a salt thereof, or a mixture thereof.

2. The method according to claim 1, wherein the dye compound is selected from the group consisting of HC Red 18, HC Blue 18, HC Yellow 16, Disperse Black 9, Acid Black 1, Disperse Orange 3, Disperse red 17, Acid black 52, Acid Red 14, Acid Orange 7, Acid Red 27, Acid Red 33, Acid Red 35, Acid Red 184, Acid Yellow 23, Acid Orange 24, Solvent Red 1, Curry Red, Acid Red 18, Pigment Red 57, salts thereof, and mixtures thereof.

3. The method according to claim 1, wherein a total concentration of the dye compound is in a range of 0.001% to 10% by weight, calculated to a total weight of the aqueous dyeing composition.

4. The method according to claim 1, wherein the alkalizing agent is triethanolamine or a salt thereof.

5. The method according to claim 1, wherein a total concentration of the alkalizing agent is in a range of 0.1% to 40% by weight, calculated to a total weight of the aqueous dyeing composition.

6. The method according to claim 1, wherein a weight ratio of the alkalizing agent to the dye compound in the aqueous dyeing composition is in a range of 0.1 to 200.

7. The method according to claim 1, wherein the aqueous dyeing composition has a pH in a range of 8.5 to 10.5.

8. The method according to claim 1, wherein a total concentration of water in the aqueous dyeing composition is 50% by weight or more, calculated to a total weight of the aqueous dyeing composition.

9. The method according to claim 1, wherein the aqueous dyeing composition further comprises an other alkalizing agent selected from the group consisting of ammonia, organic alkyl or alkanolamines having at least one basic function whose conjugate acid has a pKa above 8.0 determined by acid-base titration in water of a 0.1 M solution of the other alkalizing agent at 20° C. under atmospheric conditions, salts thereof, and mixtures thereof.

10. The method according to claim 1, wherein the aqueous dyeing composition further comprises a direct dye different from the dye compound and/or an oxidative dye.

11. The method according to claim 1, wherein the second aqueous composition comprises hydrogen peroxide at a total concentration in a range of 0.1% to 20% by weight, calculated to a total weight of the second aqueous composition.

12. The method according to claim 1, wherein the pH of the second aqueous composition is in the range of 1.5 to 5.

13. The method according to claim 1, wherein the aqueous dyeing composition further comprises a thickening polymer selected from polymers resulting in an aqueous solution and/or aqueous dispersion at a pH between 8 and 10 having a viscosity of at least 5,000 mPa·s measured at a polymer concentration of 1% by weight in water at 25° C., calculated to a total weight of the aqueous dyeing composition, determined by a Brookfield viscometer at 10 rpm for 1 min, with a spindle at 25° C.

14. A kit-of-parts, comprising:
   an aqueous dyeing composition comprising a dye compound which is an anionic azo dye, a non-ionic azo dye, a salt thereof, or a mixture thereof, and an alkalizing agent having at least one basic functional group whose conjugated acid has a pKa value in a range of 6.0 to 8.0 determined by acid-base titration in water of a 0.1 M solution of the alkalizing agent at 20° C. under atmospheric conditions,
   wherein the alkalizing agent is triethanolamine, 2-[4-(2-hydroxyethyl)-piperazin-1-yl]-ethane-1-sulfonic acid, a salt thereof, or a mixture thereof;
   a composition B comprising a direct dye selected from HC Yellow 1, 2-amino-6-chloro-4-nitrophenol, salts thereof, or mixtures thereof; and
   a second aqueous composition having a pH in a range of 1 to 6.

15. The method according to claim 1, wherein the second aqueous composition comprises hydrogen peroxide.

16. The method according to claim 1, wherein the dye compound is selected from the group consisting of HC Blue 18, HC Red 18, HC Yellow 16, Disperse Black 9, salts thereof, and mixtures thereof.

17. The method according to claim 1, wherein a total concentration of the dye compound is in a range of 0.1% to 1% by weight, calculated to a total weight of the aqueous dyeing composition.

18. The method according to claim 1, wherein the alkalizing agent is triethanolamine or a hydrochloride, sulfate, hydrosulfate, or nitrate salt thereof.

19. The method according to claim 1, wherein a total concentration of the alkalizing agent is in a range of 1% to 15% by weight, calculated to a total weight of the aqueous dyeing composition.

20. The method according to claim 1, wherein a weight ratio of the alkalizing agent to the dye compound in the aqueous dyeing composition is in a range of 10 to 75.

* * * * *